(12) United States Patent
Pisciotta (10) Patent No.: US 8,697,437 B1
(45) Date of Patent: Apr. 15, 2014

(54) MAGNETIC METABOLITE AND DIAGNOSTIC TRANSFER DISKS

(75) Inventor: John M. Pisciotta, Baltimore, MD (US)

(73) Assignee: University of South Florida, Tampa, FL (US)

(*) Notice: Subject to any disclaimer, the term of this patent is extended or adjusted under 35 U.S.C. 154(b) by 493 days.

(21) Appl. No.: 12/551,063

(22) Filed: Aug. 31, 2009

Related U.S. Application Data (60) Provisional application No. 61/092,797, filed on Aug. 29, 2008.

(51) Int. Cl.
*C12M 1/26* (2006.01)
*C12M 3/00* (2006.01)

(52) U.S. Cl.
USPC .................................. 435/309.1; 435/309.4

(58) Field of Classification Search
CPC ..................................................... C12M 23/10
See application file for complete search history.

(56) References Cited

U.S. PATENT DOCUMENTS

| | | | |
|---|---|---|---|
| 3,897,688 A | * | 8/1975 | Meserol et al. ............ 73/864.31 |
| 3,979,184 A | | 9/1976 | Giaever |
| 4,042,463 A | * | 8/1977 | Haque et al. ............... 435/252.1 |
| 4,480,031 A | | 10/1984 | Shaw |
| 4,587,213 A | * | 5/1986 | Malecki .......................... 435/39 |
| 4,634,676 A | | 1/1987 | Sapatino |
| 4,659,672 A | | 4/1987 | Provonchee et al. |
| 4,717,667 A | | 1/1988 | Provonchee |
| 5,061,621 A | | 10/1991 | Perlman |
| 5,691,195 A | | 11/1997 | Doleans et al. |
| 6,333,093 B1 | | 12/2001 | Burrell et al. |
| 6,753,180 B1 | | 6/2004 | Pisciotta |
| 7,226,733 B2 | | 6/2007 | Chan et al. |

OTHER PUBLICATIONS m-w.com entry for "grid" downloaded on Jul. 15, 2013.*

* cited by examiner

*Primary Examiner* — Hasan Ahmed
(74) *Attorney, Agent, or Firm* — Michael L. Lawson; Smith & Hopen, P.A.

(57) ABSTRACT

A magnetic, selectively permeable metabolite transfer disk for the cell-free transfer of metabolites and other molecules produced by microbial colonies is described. The metabolite transfer disk is comprised of at least three layers including: (1) an adhesion layer; (2) a gel layer comprising agar or other cushioning gel matrix; and (3) a bottom surface comprising one or more fluid-permeable filters of variable pore size to enable the diffusion of small molecules into the gel while blocking passage of cells. A diagnostic transfer disk is also described that can be used for biochemical and microbial characterization. The diagnostic transfer disk is similar to the metabolite transfer disk with the added benefit of the top layer being transparent and indicator reagents being added to the disk for microbial characterization. The diagnostic transfer disk can be altered into a wound dressing that provides for the diagnosis of human disease, namely infection, while concurrently aiding in treatment and protection of such acute injuries as lacerations or burns.

5 Claims, 8 Drawing Sheets

MAGNETIC METABOLITE AND DIAGNOSTIC TRANSFER DISKS

CROSS REFERENCE TO RELATED APPLICATIONS

This application claims priority to U.S. Provisional Patent Application 61/092,797, entitled "Magnetic Metabolite Transfer Disks and Diagnostic Transfer Disks", filed Aug. 29, 2008, the contents of which are herein incorporated by reference.

FIELD OF INVENTION

This invention relates to the cell-free transfer of metabolites and other molecules produced by microbial colonies using magnetic, selectively permeable metabolite transfer disks. This invention also relates to the use of magnetic diagnostic transfer disks that can be used for biochemical and microbial characterization.

BACKGROUND OF THE INVENTION

Cell products including metabolites and secreted enzymes such as exoenzymes are important biochemicals and enzymes that are produced by cells. Exoenzymes are any enzyme that is secreted by a cell for extracellular use. Metabolites are biochemicals produced by an organism that, unlike DNA or proteins, are not directly coded by the genome. Metabolites are common wastes like $CO_2$, ethanol and urea but they may also be complex molecules with highly specialized functions such as quorum sensing, intercellular communication, microbial allelopathy and gene regulation. (i.e. Lactose and the lac operon).

Metabolites can be divided into primary and secondary metabolites. Primary metabolites include those biochemicals that are necessary for development, growth, and reproduction of the cell. These metabolites include amino acids and nucleotides. Secondary metabolites are those biochemicals that are not essential for cell metabolism. Secondary metabolites are low-molecular weight compounds that are synthesized by only some microbial strains and are often produced in connection with differentiation processes. In addition, they are often made as families of similar products. Some secondary metabolites include antibiotics, pigments, protease inhibitors, and toxins. Some examples of metabolites include citric acid and polysaccharides, which have application in the food industry as well as glutamic acid, which is a flavor enhancer.

The most famous microbial metabolite was discovered by a legendary accident. In 1928, Alexander Fleming plated *Streptococcus* bacteria on the surface of an agar plate and placed it by the window. By chance, a fungal spore landed on the plate and grew into a colony. Metabolites produced by the fungal colony diffused through the agar and killed the nearest *Streptococcus* bacteria. Fleming recognized this antibiotic action and won the Nobel Prize for discovering Penicillin.

In addition to penicillin, many other antibiotics are considered microbial metabolites including streptomycin and cephalosporin. In addition, immunosuppressants such as Cyclosporin A and cholesterol synthesis inhibitors such as Lovastatin are also considered microbial metabolites. Microbial exoenzymes such as glutaminase and asparginase have been shown to have anti-cancer activity.

A microbial colony consists of billions of identical, metabolically active cells. The growing colony is a metabolite factory and every well-isolated colony consists of a single species of microbe. Each species colony produces its own unique mixture of metabolites. After a colony is plated, a concentration gradient of soluble metabolites diffuses outward from the colony through the agar of the Petri plate.

Our invention comprises the use of metabolite transfer disks, which enable the cell-free spatially distinct and selective transfer of soluble biological molecules that are produced by microbial cell colonies. Metabolite transfer occurs via diffusion across a selectively permeable layer on the bottom of the magnetic metabolite transfer disk that is in contact with the cell colony. The specific composition of the gel layer in conjunction with the specific type of filter used for the selectively permeable bottom layer determines what cell products (or metabolites) are taken up into the gel layer or deposited on the filter. The metabolite transfer disks of the present invention allow scientists to safely isolate and transfer microbial metabolites and other biochemicals from cell colonies grown on the surface of Petri plates.

In another embodiment of the present invention, we provide for a diagnostic transfer disk that can be used to selectively isolate cell products while obtaining a metabolic profile using different indicator reagents. For over a century different species of microbes have been identified based on their distinct metabolic profiles. The metabolic profile is dependent on specific enzymes, which can be identified by specific indicators such as enzyme substrates that care catabolized to different colored products if active enzyme is present.

An example is the Caseinase Test, which identifies cell colonies that release the exoenzyme caseinase. These caseinase-positive colonies are identified by a clear zone that forms around them when grown on opaque skim milk agar. As the secreted caseinase diffuses through the milk agar, it breaks down the white milk protein casein into colorless peptides and amino acids that can then be easily absorbed by the cells. Accordingly, the present invention can facilitate cell free transfer and identification of biomolecules like exoenzymes while also supporting cell metabolic activity from above. Inclusion of extra nutrients or inducers, such as IPTG, into the transfer disk may be used to trigger a desired activity by the colony.

Other metabolic enzymes commonly assayed for include catalase, cytochrome oxidase, beta-glucuronidase (MUG), ONPG, nitrate reduction, starch hydrolysis, etc. Metabolic enzymes are usually revealed via a color reaction. Many reactions collectively sketch a biochemical profile that identifies species and strain. Some cellular enzymes are only released when cells lyse and die.

Identification of microbial species based on composite results of a battery of biochemical tests has been used for decades. Test kits like API 20E are routinely used to identify bacteria. Cells from a colony are usually inoculated into such tests with a dropper, loop or inoculation needle. The new invention conducts multiple biochemical assays on diffusible biomolecules transferred from cell colonies into the disk. Different indicator reagents can be used on each disk due to subdividing the gel layer into separate compartments. The compartmentalization of the present invention allows many different biomolecules to be diagnosed depending on the reagent used. This embodiment of the present invention can have expanded use as a wound dressing.

U.S. Pat. No. 6,333,093 to Burrell describes a multi-layered wound dressing with a semi transparent backing. Burrell's wound dressing changes color when an alcohol or electrolyte solution is added. This color change indicates successful activation of anti-microbial compounds present in the dressing itself. While a color change can be viewed through the bandage, Burrell's patent does not relate to the diagnostic identification of microbes or metabolites. It is not a diagnostic tool, but rather it is a direct applicator of chemotherapeutics. Other such bandages have been described which, like Burrell's invention, deliver drugs or therapeutics to the wound. Importantly, however, these do not selectively recover and identify specific biochemicals from the wound for the purpose of preliminary diagnosis and indication of infection as does the present invention.

The use of "smart bandages" gained popularity between the years of 2000 to 2005. These "smart bandages" normally have an electrical component used for diagnostic purposes. For instance, Miller and Fauchet developed a sand-grain sized wafer that differentiates between Gram-positive and Gram-negative bacteria thus showing that it was possible to accurately identify bacteria with a silicon sensor.

U.S. Pat. No. 7,226,733 to Chen et. al. disclosed a biological sensor having a porous semiconductor structure comprising a central layer interposed between upper and lower layers with each of the upper and lower layers having strata of alternating porosity. The biological sensor also has one or more probes coupled to the porous semiconductor structure. A detectable change occurs in a refractive index of the biological sensor upon binding of the one or more probes to the target molecule that can then be measured through photoluminescent emissions.

One embodiment of the present invention serves a similar function as the "smart bandages"; however, the present invention need not employ advanced electronics or sensors. The lack of advanced electronics or sensors is advantageous, particularly in regions where power is not available, such as in disaster areas. Also, rather than relying on probes for binding to specific targets such as membrane-integral lipids like Lipid-A which is present in the cell membrane of Gram negative bacteria, the present invention identifies infection and causative microbes based on enzymatic conversion of exogenous substrates in the disk into colored products. Other conversion techniques such as immunochromatographic antibody binding and metabolite dependent pH changes can be incorporated into the biochemical/microbial characterization wound dressing as well as the diagnostic transfer disks of the present invention. Unlike electronic bandages, these relatively simple techniques are generally known to those of ordinary skill in the art of microbiology.

The inventive device significantly advances the overall utility and demand for metabolite disks as well as provides new specialty transfer disks reported here for the first time. Cell free transfer of microbial cell colony metabolites via magnetic transfer disks is new and unobvious as is in-disk metabolic characterization and species identification and diagnosis. These features greatly expand the utility of the invention.

SUMMARY OF INVENTION

In one embodiment of the present invention, a metabolite transfer disk is provided that is comprised of at least three layers: an adhesion layer; at least one gel layer; and a bottom surface layer that is comprised of at least one fluid-permeable filter.

The adhesion layer is preferably fluid-impermeable in order to contain the metabolites in the gel layer. It is also preferred that the adhesion layer is comprised of a ferromagnetic material to attach to the magnetic base of the clonal replicator.

The gel layer is preferably comprised of a gel cushioning matrix. The gel cushioning matrix includes but is not limited to such gels as agar, hydrogels, and aerogels. A honeycomb grid can be provided that is comprised of fluid-impermeable flexible vertical walls. The grid is placed into the gel layer to subdivide the gel layer into separate compartments, which allows for concentration and isolation of the metabolites that diffuse upwardly from the plate below. The grid functions to prevent the lateral spread of metabolites and to provide visible demarcation of metabolite plate position relative to the known plate position of the parent cell colony. If multiple gel layers are employed, the grid further functions to provide structural adherence between the gel layers. Optionally, the grid can be continuous with the adhesion layer, which would further anchor the gels to the disk.

The bottom surface layer is preferably comprised of at least one fluid-permeable filter. Preferably, the fluid-permeable filter is comprised of variable pore sizes to allow passage of small molecules into the gel while blocking the passage of cells thereby keeping the cells on the Petri plate.

Optionally, in order to maintain the structural integrity of the disk, the filter can be comprised of a material that extends upwardly around the peripheral circumference of the disk. This material can then be affixed to the magnetic adhesion layer. If this embodiment is chosen, a secondary filter having a diameter equal to the inner diameter of the Petri plate can be reversibly affixed to the bottom surface layer to allow the filter to remain on the plate via surface tension during magnetic recovery of the disk.

A second preferred embodiment of the present invention is a diagnostic transfer disk. This embodiment preferably is comprised of an adhesion layer; a grid having impermeable vertical walls; at least one gel layer; at least one indicator substance; and a bottom surface layer that is further comprised of at least one fluid permeable filter having variable pore sizes.

In this embodiment, the adhesion layer is preferably fluid-impermeable and transparent. Preferably, the transparent material is plastic. The transparency of this top layer allows for diagnosis of infection or disease after the indicator substance is added to the gel layer containing the metabolites or other small molecules. Similarly, to the metabolite transfer disks, this top layer can be comprised of a ferromagnetic material to attach to the magnetic bottom of the clonal replicator. Preferably, the adhesion layer contains a peripheral ferromagnetic ring.

As with the metabolite transfer disks, the grid of the diagnostic transfer disks functions to subdivide the gel layer into individual compartments. The gel layer is preferably comprised of a hydrogel, an aerogel, agar, or other suitable cushioning gel matrix. The grid is preferably comprised of flexible impermeable vertical walls, which block the lateral diffusion of metabolites and other small molecules across the disk while allowing for upward diffusion of the molecules/metabolites from the cells on the plate into the gel layer. The grid may be comprised of a non-reactive ferromagnetic material that is continuous with the adhesion layer to promote structural integrity of the disk.

Preferably, the indicator substances are contained within, or later applied to the disk. The indicator substances can be reagents, labeling antibodies, enzymes, or chemical reactants.

A third embodiment of the present invention is a wound dressing that provides for the diagnosis of disease or infection while concurrently aiding in treatment and protection of acute injuries. The wound dressing is comprised of a transparent backing layer; a grid; at least one gel layer; at least one indicator substance; a bottom surface layer comprised of at least one fluid-permeable filter having variable pore size; and a sterile gauze layer.

Preferably, the top transparent backing layer allows for visualization of the metabolization of the indicator substance with the microbe or metabolite. The transparent backing layer is preferably flexible and fluid impermeable to allow for placement on a wound without risk of outside contamination.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The present invention represents an improvement over the prior art. In one embodiment, the invention enables cell-free transfer of selected metabolites and other molecules produced by microbial colonies using magnetic, selectively-permeable metabolite transfer disks. In a related embodiment, the invention is a diagnostic transfer disk that is useful in biochemical and microbial characterization. A third embodiment is a wound dressing that allows for direct metabolic and microbiological in-gel analysis while concurrently protecting the wound area.

The present invention is an improvement to our previously patented clonal replication system (U.S. Pat. No. 6,753,180), incorporated herein by reference. The clonal replication system was originally conceived as a handheld lab device used to safely lift and transfer biological entities, namely microbial cell colonies, from the surface of Petri plates to allow them to be easily sub-cultured to new plates without contamination. This was a significant problem with the existing technology at the time. The invention accomplished its objectives through reversibly attachable, fluid impermeable, cushioned Clonal Transfer Disks.

"Transfer Disks" as defined herein include the Clonal Transfer Disks described above as well as the Metabolite Transfer Disks and the Diagnostic Transfer Disks of the present application.

Figure 1:
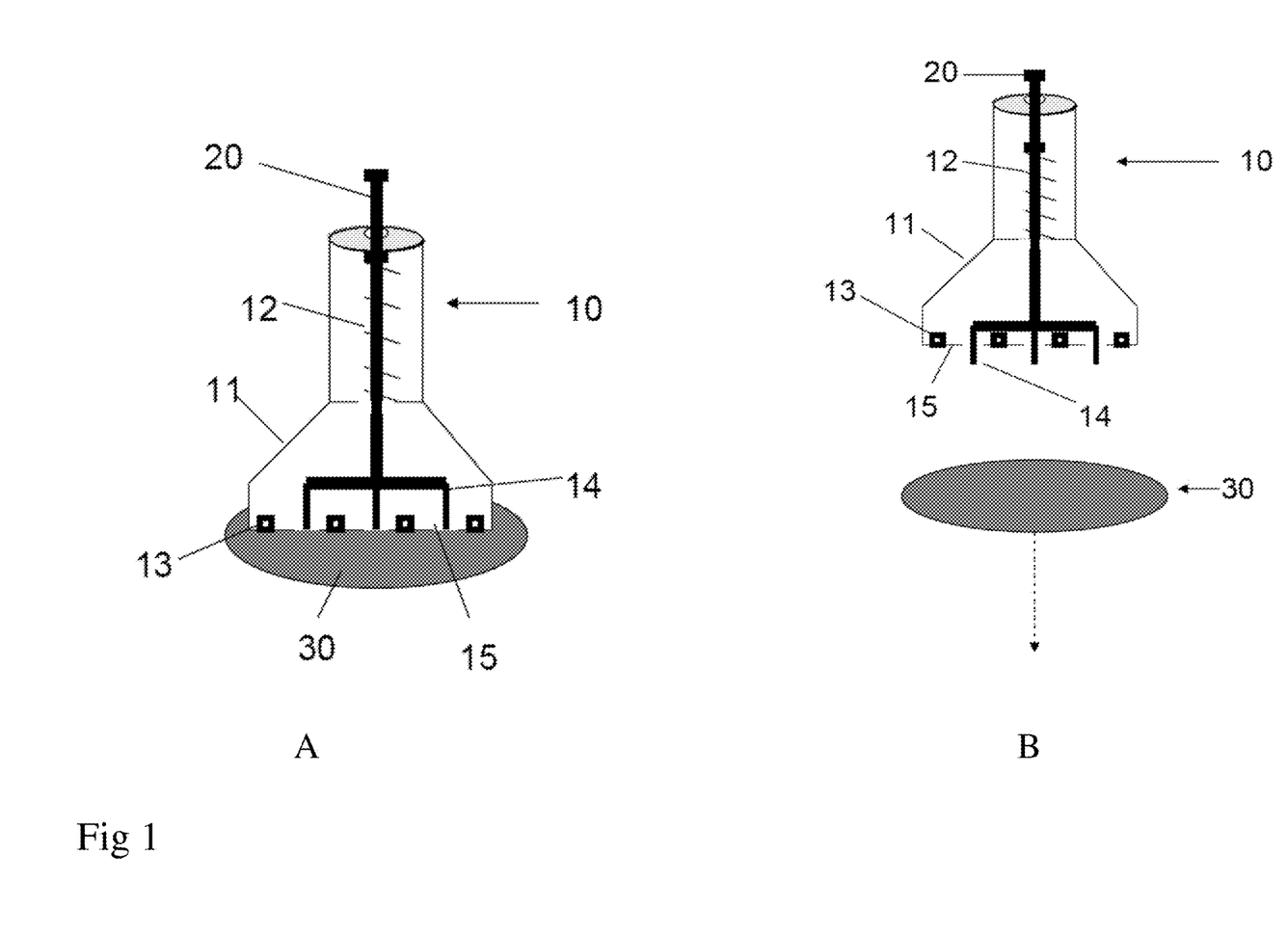
FIG. 1 is a diagram showing the improved clonal replicator device specifically illustrating the ejector mechanism. (A) shows the default position of the improved clonal replicator with the magnetic disk attached. (B) shows the magnetic disk detachment by the prong separators.

The present invention improves on the previous clonal replication system (U.S. Pat. No. 6,753,180) by providing a handheld clonal replicator 10 that is equipped with a magnetic base and ferromagnetic transfer disks for instantaneous attachment of Transfer Disks. As shown in FIG. 1A, Replicator 10 is also equipped with a disk ejector mechanism 20 as opposed to the older use of Velcro disk attachment means. The disk ejector mechanism 20 is equipped with a spring 12, which is housed within the body housing 11 of the replicator 10.

Alternatively, an electromagnetic ejector mechanism can be used in order to more easily switch N/S polarity and regulate power. For example, magnetic antibody-coated beads can be integrated into the gel near the filter. If these beads need to be pulled up through different gel layers, they would bind up and thereby concentrate more of the targeted metabolite (antigen) prior to interacting with an indicator located in an upper portion of the disk. In cases like this, a low power setting is used to transfer the disk. One or higher power settings can cause on-demand movement of the magnetic beads inside the gel layers.

The base 15 of the replicator 10 contains one or more magnets 13, which function to adhere the ferromagnetic disks 30 of the present invention to the replicator 10. The ejector mechanism 20 extends downward through the body housing 11 to attach to a release mechanism 14, which function to remove the disk 30 from the replicator 10 as shown in FIG. 1B. Preferably, the release mechanism is a plurality of prong separators. This improves safety, ease of use and throughput while also reducing the likelihood of cross-contamination compared to alternative methods. This is because the operator need never touch the transfer disks since their attachment and release is automatic and instantaneous. The replicator base diameter has been reduced thus enabling access to all sizes of Petri Plates. Different-sized transfer disks are lifted by the same handheld replicator. Disks may be mass-produced by punching them out of a layered sheet.

Figure 2:
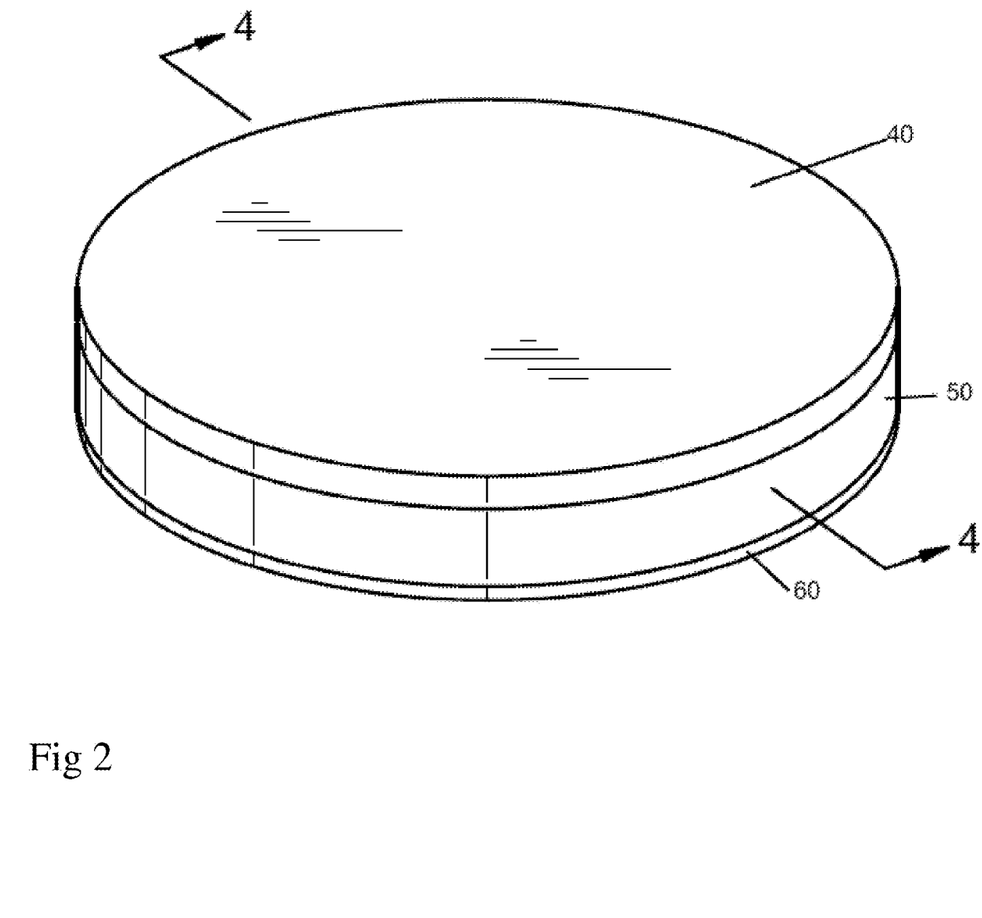
FIG. 2 is a diagram of the Metabolite Transfer Disks and Diagnostic Transfer Disks of the present invention.
Figure 3:
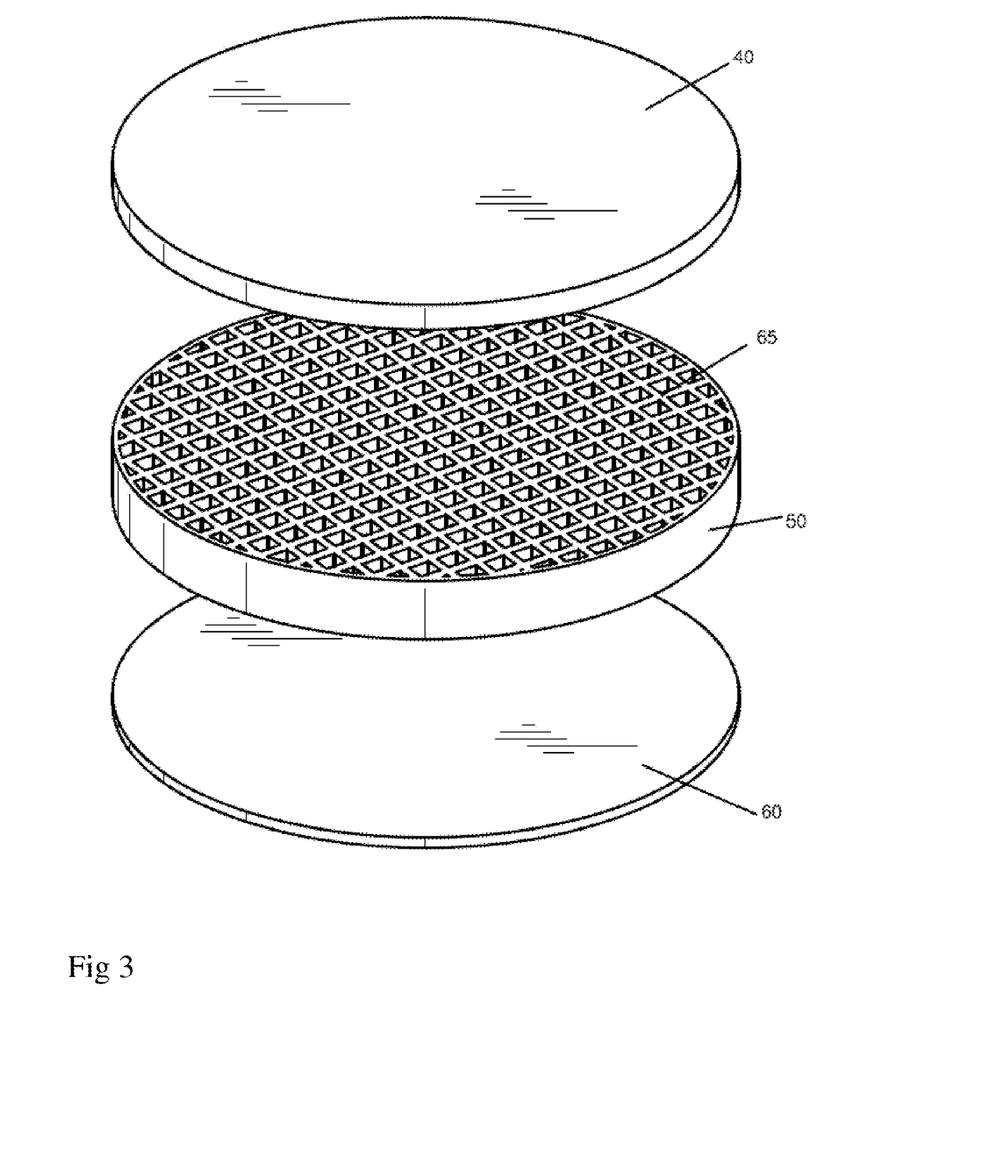
FIG. 3 is an exploded view of the Metabolite Transfer Disk and/or the Diagnostic Transfer Disk showing the layers of the disk.

Embodiments of the present invention include the use of ferromagnetic, selectively-permeable, gel-cushioned "Metabolite Transfer Disks" and "Diagnostic Transfer Disks" which expand the utility of the handheld replicator 10 beyond sub-culturing of cell colonies. The Metabolite Transfer Disks 30 allow for the cell-free transfer of metabolites. The Metabolite Transfer Disks 30 are comprised of at least three layers. The Metabolite Transfer Disks 30 consist of a top magnetic adhesion layer 40, which is used to adhere the disk 30 to the clonal replicator 10. The middle gel layer 50 consists of agar or other cushioning gel matrix. A honeycomb or grid 65 of impermeable flexible walls subdivides the middle gel layer 50 into compartments 85 thus enabling the metabolites to remain isolated and concentrated over time. The bottom surface layer 60 consists of one or more fluid-permeable filters of variable pore size to enable the diffusion of small molecules into the disk 30 while blocking passage of the cell into the disk 30.

The Diagnostic Transfer Disks 35 are also comprised of at least three layers, similar to the Metabolite Transfer Disks 30. Diagnostic Transfer Disks 35 differ from other disk types in that the backing of the magnetic adhesion layer 40 is transparent and one or more specific indicator reagents or labeled antibodies are included in, or later applied to, the disk 35. As with Metabolite Transfer Disks 30 the middle gel layer 50 employs an impermeable grid 65 to sub-divide the middle gel layer 50 into multiple, isolated compartments 85. Each compartment 85 of the middle gel layer 50 houses a different indicator reagent so that if a microbe has the appropriate enzyme, the colorless substrate is metabolized into a colored product. Each disk 35 contains a plurality of distinct compartments 85 enabling a plurality of different biochemical reactions to be conducted and visually monitored through the transparent backing of the adhesion layer 40 to obtain a diagnostic profile. Diagnostic Transfer Disks 35 enable identification of bacterial species grown evenly over the surface of a Petri plate based on specific biochemical reactions that take place within isolated compartments 85 viewable inside the Diagnostic Transfer Disk 35. These features mark a significant, non-obvious supplementation to the Cell Colony Transfer Disk described by the original patent. All three types of Transfer Disks are fully compatible with the handheld magnetic clonal replicator 10.

Example 1

Metabolite Transfer Disk

A microbial colony consists of billions of identical, metabolically active cells; the growing colony is a metabolite factory. Every well isolated colony consists of a single species of microbe. Each species' colony produces its own unique mixture of metabolites. A concentration gradient of soluble metabolites diffuses outward from the colony through the agar of the Petri plate. The present invention allows these metabolites to diffuse into the disk 30 for later analysis while the actual cell colonies remain on the agar plate.

Metabolite Transfer Disks 30 enable cell-free, spatially distinct and selective transfer of soluble biological molecules produced by microbial cell colonies. Metabolite transfer occurs via diffusion across a selectively permeable layer on the bottom of the disk. The specific combination of filter used as the bottom surface layer 60 in conjunction with the composition of the gel layer 50 defines which cell products are uptaken into the disk 30. Metabolite Transfer Disks 30 allow scientists to safely isolate and transfer microbial metabolites and other biochemicals from cell colonies grown on the surface of Petri plates and are useful for the purpose of antibiotic drug discovery.

The composition of the Metabolite Transfer Disks 30 is shown in FIGS. 2 and 3. Metabolite Transfer Disks 30 are comprised of at least three layers: a top magnetic adhesion layer 40, a middle gel layer 50, and a bottom (base) surface layer 60. The top layer 40 is an adhesion layer that is used to adhere the Metabolite Transfer Disk to the base of the clonal replicator 10. The top adhesion layer 40 is preferably comprised of a ferromagnetic material to be compatible with the magnetic base of the clonal replicator 10. The top adhesion layer 40 may have a ferromagnetic ring around the periphery of the disk 30 for attachment to the clonal replicator 10.

The second (middle) layer 50 is a gel layer consisting preferably of agar, hydrogel, aerogel, or another cushioning gel matrix. The composition of the middle gel layer 50 assists in determining the particular types of cell products/metabolites that are diffused upwards into the disk 30 from the agar plate. If isotonic agar is used the rate of metabolite diffusion into the disk 30 is the same as the rate of metabolite diffusion through the original agar Petri plate.

Altering gel composition enables selective metabolite uptake. For instance, hydrophobic gels can be used to selectively uptake hydrophobic cell products. Alternatively, increasing the gel layer's salt content favors osmosis (flow of water) into a relatively hypertonic disk. This enables selective uptake and transfer of water-soluble hydrophilic metabolites, which move with the water. To prevent transmission of salt ions through the filter to the colonies, silica gel could alternatively be used as this material absorbs up to 40 times its weight in water. It also reduces weight and size of disks by reducing pre-use water content. Gel pH may be adjusted so as to selectively uptake acidic or basic metabolites. An activated carbon layer near the filter may be used to adsorb certain metabolites while allowing others such as strong acids or bases to pass deeper into the gel. In addition, the application of a charge differential between an electrically conductive filter (anode) and an electrically conductive impermeable top layer (cathode) further separates metabolites vertically based on charge once in/on disk. Reversing polarity separates positive and negative charged metabolites.

Figure 4:
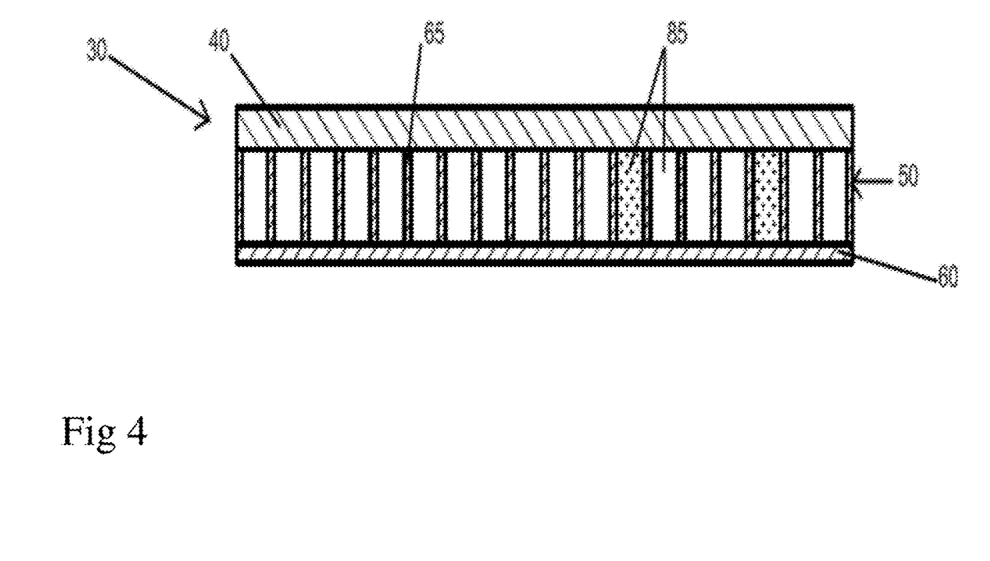
FIG. 4 is a cross-sectional view of the Metabolite Transfer Disk showing the compartments of the gel layer.

FIG. 4 shows a cross-section of the Metabolite Transfer Disk of the present invention. A grid 65 having fluid-impermeable walls is inserted into the gel layer 60 to compartmentalize the metabolites. The grid 65 is preferably flexible and in a honeycomb shape. The compartmentalization effectuated by the grid 65 prevents lateral diffusion across disk 30 and serves to isolate and concentrate the metabolites or other cell products that have diffused into the gel layer 50 of the disk 30. In some cases, lateral diffusion of cell products would be useful and thus the grid 65 is not necessary. For example, in gel immunoprecipitation-based identification plus quantification of a cell product, such as a bacterial toxin (antigen), a transfer disk devoid of a grid 65 may be used. In such an instance, lateral diffusion of the cell product would be useful.

The third layer is a bottom surface layer 60 that consists of one or more fluid-permeable filters. These filters can be of variable pore size to enable the diffusion of small molecules into the gel while blocking passage of cells. Different types of membrane filters can be used to exclude some cell products from the disk 30 while admitting other cell products to the disk 30. For instance, even if the gel layer 50 has a hydrophobic composition that would invite all hydrophobic cell products to diffuse into the gel layer 50, a specific filter may be used that selectively uptakes and transfers only small hydrophobic cell products into the gel layer 50. The larger hydrophobic cell products are left on the Petri plate with the original cell colonies or accumulate on the exterior of the filter. Hydrophobic filter membranes are often polydimethylsiloxane based.

Changing the filter material allows the user to selectively alter metabolite or cell product uptake. Many types of filters can be used with the present invention. Specific filters are well known by those of ordinary skill in the art. For instance, nitrocellulose filters bind proteins and filter them out prior to gel entry. The filters can be probed later by antibody-based methods for specific proteins that would thus accumulate on the filter. There are also filters that selectively pass the common respiration metabolite $CO_2$ but blocks $H_2$. The above illustrations are merely exemplary and are not to be interpreted to in any way limit the present invention.

The composition of the gel layer 50 along with the type of filter used in the bottom surface layer 60 selectively determines what particular cell products are diffused into the disk 30. Many gel/filter combinations are possible according to what particular cell products need to be analyzed.

In addition, structural integrity can be maintained by the filter, provided filter material extends up around peripheral circumference of the disk and is affixed to magnetic adhesion layer 40 (Nylon ideal). In addition, if this configuration is used, a reversibly affixed secondary cell filter having the inner diameter of the Petri plate is on the bottom layer 60 so that it may be left on the plate via surface tension during magnetic recovery of disk 30. This is useful for antibody dot blots, DNA binding experiments, or storage as a cell hardcopy.

Figure 5:
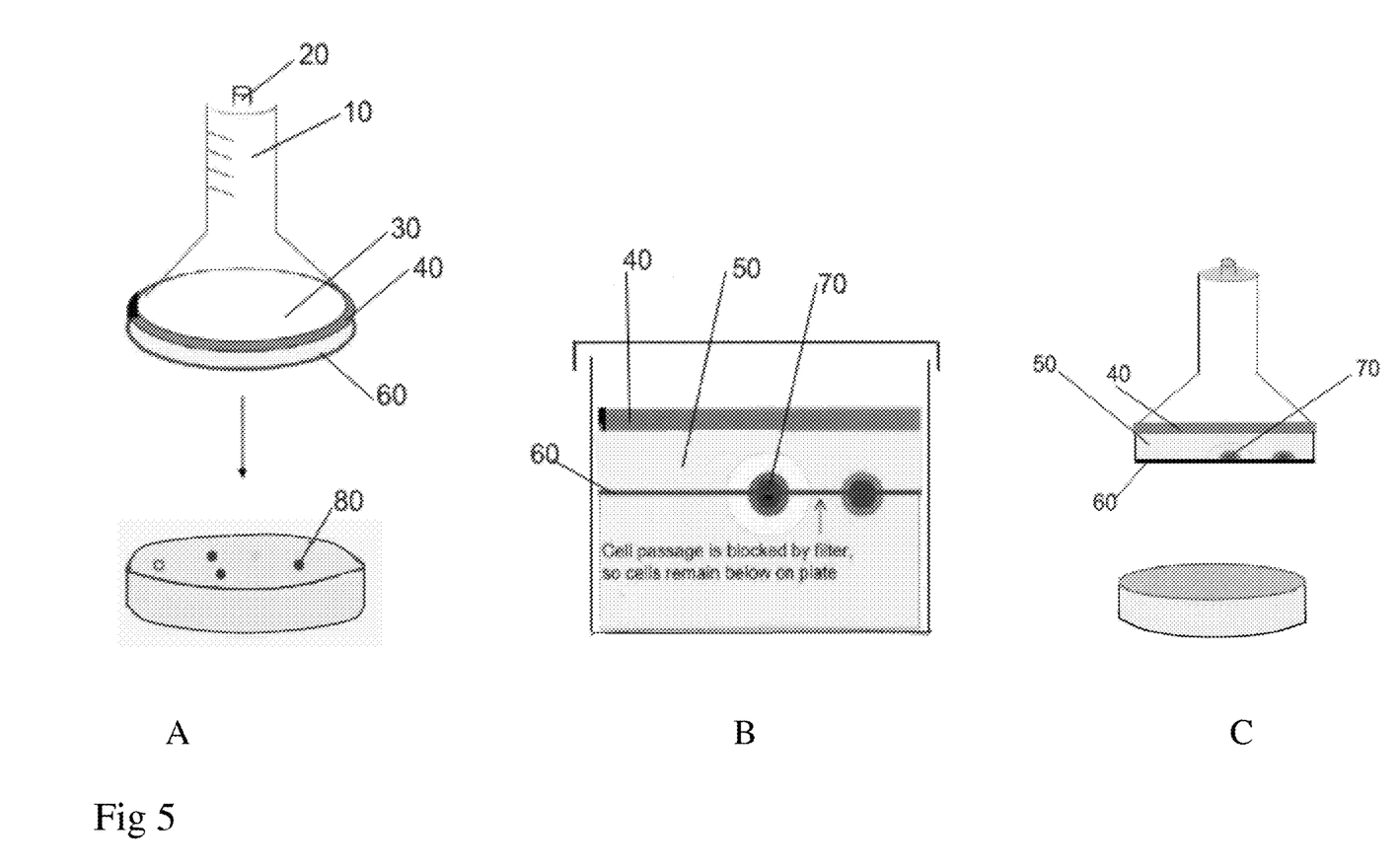
FIG. 5 is a diagram illustrating colony-specific metabolite transfer via a specialized disk according to one embodiment of the present invention. (A) shows the clonal replicator applying the disk to the plate at any time after the cells have been plated. (B) shows that during incubation, metabolites pass through the filter into the gel layer while cells remain on the plate. (C) shows the magnetic recovery of the disk.
Figure 6:
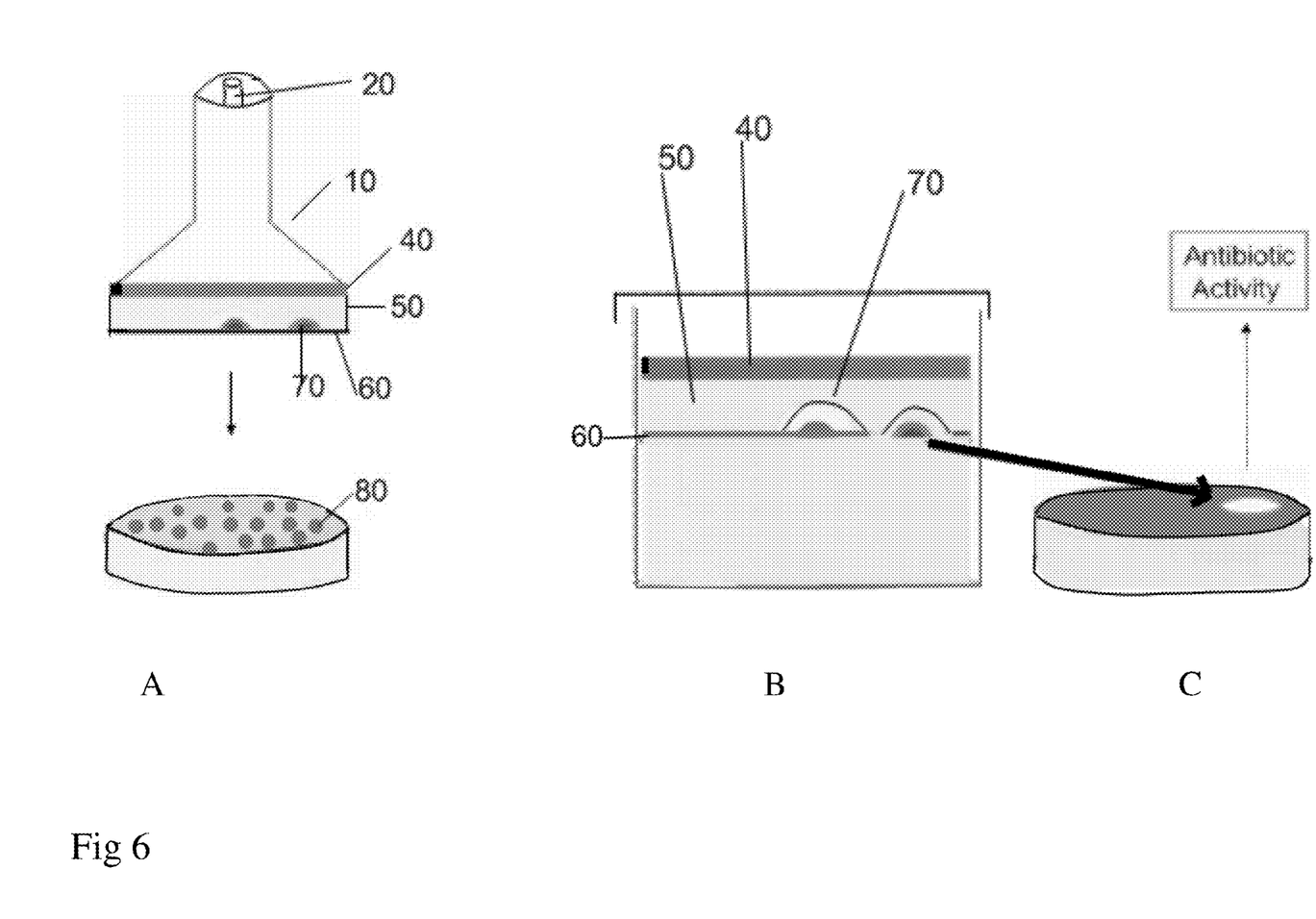
FIG. 6 is a diagram illustrating a potential use of the present invention: antibiotic discovery. (A) shows the magnetic disk being applied over a dilute lawn of pathogenic cells. (B) shows the disk being incubated to grow the cell lawn in the presence of the transferred metabolites. (C) shows antibiotic inhibition as seen by holes in the cell lawn.

FIGS. 5 and 6 illustrate proposed methods of using the inventive Metabolite Transfer Disks 30. The cell-free transfer of colonies is shown in FIG. 5. In the first step, the cells are plated onto an agar plate. Next, the Metabolic Transfer Disk 30 is magnetically attached to the base of the clonal replicator 10. Anytime after the cells are plated, the Metabolic Transfer Disk 30 can be applied to the top of the agar medium within the plate. The metabolites diffuse upwardly through the filter in the bottom surface layer 60 and up into the middle gel layer 50 of the disk 30. Cell passage is blocked by the filter resulting in the cells remaining on the plate. The disk 30 is incubated for the desired amount of time after which the disk 30 is magnetically recovered and surface tension removes the disk from the clonal replicator.

FIG. 6 illustrates the use of the Metabolite Transfer Disks 30 in antibiotic drug discovery. The incubated Metabolite Transfer Disk 30 is attached to the clonal replicator 10 and is placed over an evenly plated, dilute lawn of pathogenic cells. The disk 30 and plate are incubated to grow the cell lawn in the presence of the transferred metabolites. Antibiotic activity against the pathogen cells is revealed as holes or zones of clearing in the cellular lawn. The disk 30 itself can also be inverted and directly plated to if agar is used as the gel matrix.

Example II

Diagnostic Transfer Disk

It is commonly known by those in the art that different species of microbes can be identified based on their distinct metabolic profiles. The metabolic profile is dependent on specific enzymes and researchers apply reagents that they can easily monitor for enzymatic activity. On of the simplest examples is the Catalase Test in which $H_2O_2$ (hydrogen peroxide) is applied directly to the cell colony. If catalase is present, this is revealed by bubble formation as metabolites water and $O_2$ are produced.

Many reactions collectively sketch biochemical profile that identifies species and strain. Other metabolic enzymes commonly assayed for include cytochrome oxidase, beta-glucuronidase (MUG), ONPG, Nitrate reduction, starch hydrolysis, etc. Metabolic enzymes are usually revealed via color reaction.

Diagnostic Transfer Disks 35 function similarly to Metabolite Transfer Disks 30 but one or more specific indicator reagents or labeled antibodies are included in, or later applied to, the disk 35. Those of ordinary skill in microbiology commonly know indicator reagents, antibodies, color reactions and enzymes. Reactions are viewed from the top or the bottom of the disk 35. Importantly, since each disk 35 has multiple isolated compartments 85 multiple different reagents can be assayed for per each disk 35. Here a mono-species "lawn" plate may serve as the template.

The Diagnostic Transfer Disk 35 is also comprised of at least three layers similar to the Metabolite Transfer Disk 30: a top magnetic adhesion layer 40, a middle gel layer 50, and a bottom surface layer 60. The top magnetic adhesion layer 40 of the disk is transparent in order to enable diagnosis of infection/disease. Preferably, the top adhesion layer 40 is impermeable. In a preferred embodiment, the impermeable top layer 40 is comprised of a transparent plastic.

The middle gel layer 50 is compartmentalized by a vertical grid 65. This vertical grid 65 may be of a non-reactive, ferromagnetic material so that the grid 65 functions in both gel compartmentalization and magnetic attachment to replicator 10. Alternatively, a peripheral ferromagnetic ring may function in magnetic replicator attachment.

Figure 7:
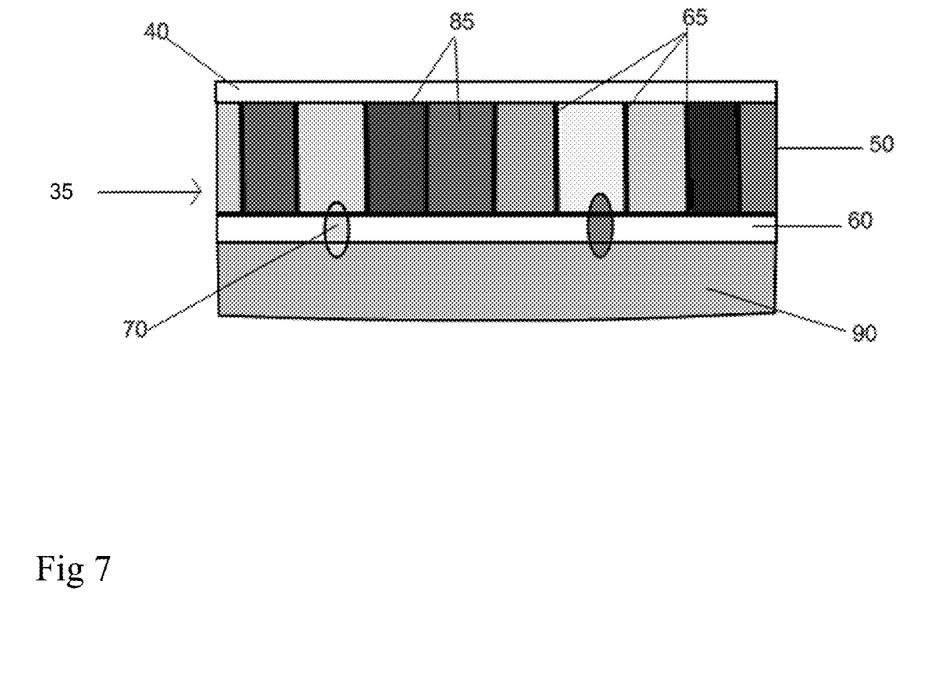
FIG. 7 is a cross-sectional view of a Diagnostic Transfer Disk illustrating the walled compartments of the gel layer. Each compartment can contain a different indicator reagent to allow for identification of a specific metabolite.

The walled compartmentalization of colony metabolites can be seen in FIG. 7, which depicts a cross-section of the Diagnostic Transfer Disk 35. A honeycomb or grid 65 of impermeable, flexible walls subdivides gel layer 50 into compartments 85. Metabolites diffuse up from the plate below but not laterally across the disk 35, so metabolites remain isolated and concentrated over time. The grid 65 provides visible demarcation of metabolite plate position, as by a quadrant system, to allow tracking of metabolite position relative to known plate position of the parent colony. If selective disks 35 of multiple different gel layers 50 are desired, then the grid 65 aids in structural adherence between gel layers 50. Structural integrity can be achieved through adhering the grid 65 to the magnetic adhesion layer 40 so that the grid 65 is continuous with magnetic adhesion layer 40. Adhering the grid 65 to the magnetic adhesion layer 40 has the added benefit of anchoring the gels to the disk 35.

Antimicrobial susceptibility testing against multiple drugs and drug concentrations can be tested on a monotypic spread plate for strain speciation if each compartment 85 contains a different drug or concentration thereof. Here the disk 35 acts as a multi-drug applicator as drugs diffuse out from the disk 35. If gel layer 50 is of nutrient type agar transferred cells may be grow directly on disk 35.

FIG. 7 illustrates the Diagnostic Transfer Disk 35. The cells grown on the agar plate 90 to form a uniform monolayer lawn. The Diagnostic Transfer Disk 35 is placed on the lawn with the bottom surface layer 60 in direct contact with the lawn. Due to the cell monolayer, there is uniform distribution of all soluble microbe metabolites and enzymes in all gel layer compartments 85. Each compartment 85 houses a different indicator reagent. If a microbe has the appropriate enzyme, the compartment's colorless substrate is metabolized into the colored product, which can be viewed through the fluid-impermeable transparent top layer 40. The overall combination of metabolic results identifies the microbe species.

The bottom surface layer 60 of the Diagnostic Transfer Disk 35 functions similarly to that of the Metabolite Transfer Disk 30. The bottom surface layer 60 is comprised of at least one filter that functions to selectively permit uptake of different cell products. Similarly to the Metabolite Transfer Disks 30, the combination of the composition of the gel layer 50 with the specific type of filter used in the bottom surface layer 60 determine the type of metabolites or cell products that are drawn into the Diagnostic Transfer Disks 35.

Various types of filters can be used in conjunction with the present invention. Nitrocellulose filters, for example, bind proteins and filter them out prior to gel entry. If proteins are to be analyzed then nitrocellulose filters should be avoided in order to enable soluble enzyme transfer to disks since enzymes (proteins) bind nitrocellulose. If membrane-bound enzymes are used then the filter pore size should be enlarged.

Ceramic filters are another type of filter that is typically used to separate metabolites such as ethanol while blocking the passage of water. If this type of filter is paired with a gel layer 50 such as an aerogel, then the cell metabolite ethanol can be selectively isolated via the process of pervaporation. Refrigerating the disk 35 subsequent to the allotted transfer time period causes the ethanol vapor in the aerogel to condense on the chilled transparent top layer 40 so that ethanol-producing isolates can be quickly identified by the ethanol condensation pattern on the transparent top layer 40. The metabolite can then be drawn off for further testing. Since water is poorly transferred from the growth media agar, the hydrated growth media will dry out less rapidly than normal, which would be useful in slow-growing cultures.

Alternatively, the Aerogel cushion layer could take the form of an air-filled void and the transparent top layer 40 can take the form of the Petri plate lid. For some anaerobic cultures, for instance certain anaerobic cellulose-degrading ethanol producers such as *Clostridium phytofermentans*, the air could be removed from this void via a pumping means and the disk sealed. This vacuum facilitates the pervaporative metabolite transfer process as described above and also enables strict anaerobes to grow.

Further applications of this embodiment include: compartmentalized and flexible metabolite transfer head or wristbands to reveal metabolic abnormalities in metabolites like lactate through sweat; diagnostic dressings, bandages or tissues; and bio-defense or food QC inception through the use of filter-less selective and/or differential nutrient disks, which can lift microscopic cells directly from surfaces for direct incubation and results.

Example 3

Biochemical/Microbe Characterization Disk as Wound Dressing

Figure 8:
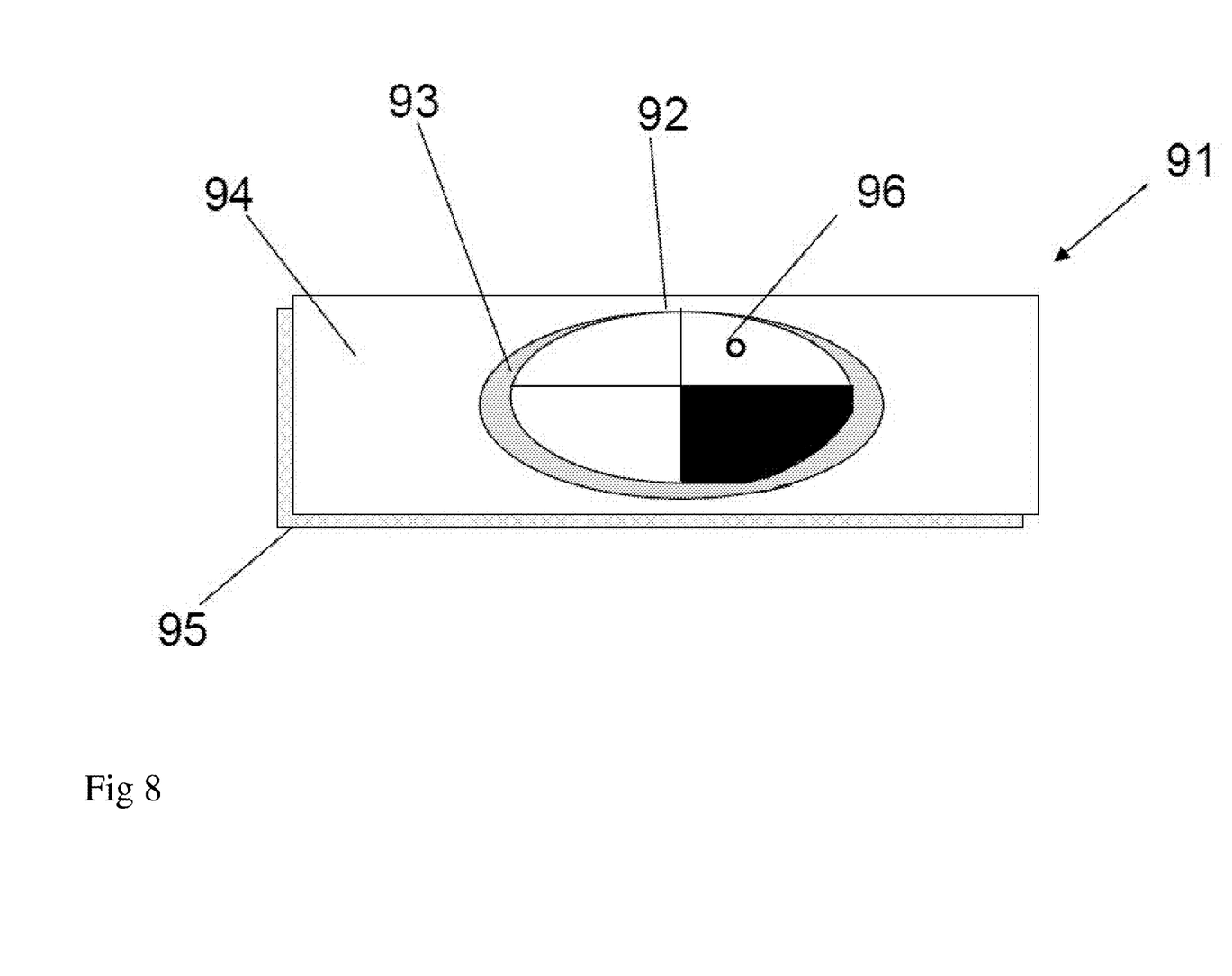
FIG. 8 is a diagram of the biochemical/microbial characterization wound dressing according to one embodiment of the present invention.

As discussed above, the use "smart bandages" has gained popularity in recent years. The present invention represents an improvement over the prior art. The Diagnostic Transfer Disks 35 discussed above can be easily adapted into Biochemical/Microbe Characterization Disks 91 that can be used as a wound dressing. The Biochemical/Microbe Characterization Disks 91 are similar to the Diagnostic Transfer Disks 35 described above in that they are comprised of at least three layers: a top layer 92, a middle gel layer 93, and a bottom surface layer 94. Preferably, a sterile gauze type layer 95 overlays the bottom surface layer 94. The top layer 92 is preferably flexible and transparent. The invention provides for the diagnosis of human disease, namely infection, while concurrently aiding in treatment and protection of such acute injuries as lacerations or burns. In this capacity, the device possesses direct access to human blood, lymph fluid, and pus from the wound site. This is an ideal position for direct metabolic and microbiological in-gel analysis (as described in detail above) while concurrently protecting the wound area. The present invention also preferably includes an access port 96 through which medicine can be administered or samples recovered without removing the wound dressing/bandage. Drugs can be incorporated into the wound dressing's gel layer in order to both help treat infections but also to facilitate functioning of the invention as diagnostic bandage of antibiotic resistant bacteria. For example, if *Staphylococcus aureus* is indicated by a diagnostic bandage amended to contain and deliver an antibiotic such as methicillin to a burn or wound then this may indicate the presence of methicillin-resistant *Staphylococcus aureus* (MRSA) more rapidly than traditional laboratory culture methods.

Erythrocytes or red blood cells (RBCs) impart the red color to blood. RBCs are of roughly 6 μM in size and thus are prevented from entering the diagnostic (middle gel) layer 93 by the sub-micron filter (bottom surface) layer 94. This is necessary for accurate color determination in the reaction wells when viewed from above. Serum is of a clear to faint yellow color and so is compatible with most color based diagnostic tests such as enzymatic assays. Indeed, entry of serum can be advantageously exploited by the integration of highly specific immunochromatographic reaction chambers in the gel layer 93.

Since RBCs are prevented entry through the cell filter, a sterile gauze layer 95 must overlay the sub-micron cell filter (bottom surface layer) 94. This prevents the wound dressing from sliding on the skin and also aids in blood clotting while protecting the filter from mechanical stresses and rupture.

Compartment specific color changes within the wound dressing's individual gel compartments are viewed through the top transparent backing layer 92. This flexible, impermeable layer also serves to block entry of outside microbes through the wound dressing/bandage but may permit gas exchange to prevent growth of anaerobic pathogens such as *Clostridium perfringens*, causative agent of gas gangrene. This device provides a first indication of infection and means of diagnosis without need for removal of the wound dressing/bandage itself, which facilitates healing. The wound dressing/bandage also assays for metabolites that indicate when changing of the wound dressing/bandage is required.

Because wounds and burns are common sites of microbial infection and because microbial cell density is correspondingly greatest at the infected injury site this diagnostic wound dressing/bandage is the ideal means of identifying infections at the earliest possible stage. Early identification of infection with pathogen identification is important in determining course of treatment and patient prognosis.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention, which, as a matter of language, might be said to fall there between. Now that the invention has been described,

What is claimed is:

1. A diagnostic transfer disk comprising:
   a top fluid-impermeable transparent adhesion layer capable of being removably affixed to a clonal replicator, wherein the adhesion layer is comprised of a peripheral ferromagnetic ring;
   at least one middle gel layer disposed adjacent to the top fluid-impermeable transparent adhesion layer, wherein the at least one middle gel comprises a cushioning gel matrix;
   a grid disposed within the at least one middle gel layer, comprising lateral fluid-impermeable vertical walls to subdivide the middle gel layer into fully separated, enclosed compartments and to prevent the migration of cell products between the compartments;
   at least one indicator substance contained within at least one of the compartments of the middle gel layer; and
   a bottom layer comprising at least one fluid-permeable filter of variable pore size;
   whereby the at least one fluid-permeable filter supports the at least one middle gel layer;
   whereby the at least one fluid-permeable filter is placed in contact with cells located on a surface;

whereby the at least one fluid-permeable filter uptakes the cell products and the metabolites to diffuse the cell products and the metabolites into the middle gel layer while the cells are blocked by the at least one fluid-permeable filter;

whereby the top fluid-impermeable transparent adhesion layer allows a user to view the cell products and the metabolites that have diffused upwards into the middle gel layer for diagnosis;

whereby the grid provides visible demarcation of metabolite plate position using a quadrant system to allow tracking of metabolite position relative to known plate position of a parent colony.

2. The diagnostic transfer disk of claim 1 wherein the cushioning gel matrix is selected from the group consisting of agar, hydrogel, and aerogel.

3. The diagnostic transfer disk of claim 1, wherein the vertical grid is comprised of a non-reactive ferromagnetic material.

4. The diagnostic transfer disk of claim 1, wherein the grid is continuous with the adhesion layer.

5. The diagnostic transfer disk of claim 1, wherein the indicator substance is selected from the group consisting of an indicator reagent, a labeling antibody, an enzyme, or a chemical reactant.

* * * * *